(12) United States Patent
Erfan et al.

(10) Patent No.: US 9,011,830 B2
(45) Date of Patent: Apr. 21, 2015

(54) POLY(CPP-SA) ANHYDRIDE AS A REACTIVE BARRIER MATRIX AGAINST PERCUTANEOUS ABSORPTION OF TOXIC CHEMICALS

(76) Inventors: Mohammad Erfan, Tehran (IR); Hamid Reza Moghimi, Tehran (IR); Azadeh Haeri, Tehran (IR); Tahereh Sadat Jafarzadeh Kashi, Tehran (IR); Farhad Jafarzade, Santa Clara, CA (US)

( * ) Notice: Subject to any disclaimer, the term of this patent is extended or adjusted under 35 U.S.C. 154(b) by 358 days.

(21) Appl. No.: 13/422,874

(22) Filed: Mar. 16, 2012

(65) Prior Publication Data
US 2012/0237471 A1    Sep. 20, 2012

Related U.S. Application Data

(60) Provisional application No. 61/453,640, filed on Mar. 17, 2011.

(51) Int. Cl.
| | | |
|---|---|---|
| *A61K 31/775* | (2006.01) | |
| *A61P 17/00* | (2006.01) | |
| *C08G 63/66* | (2006.01) | |
| *C08L 73/02* | (2006.01) | |
| *A61K 9/00* | (2006.01) | |
| *A61K 47/14* | (2006.01) | |
| *C08G 67/04* | (2006.01) | |

(52) U.S. Cl.
CPC .............. *A61K 31/775* (2013.01); *C08L 73/02* (2013.01); *A61K 9/0014* (2013.01); *A61K 47/14* (2013.01); *C08G 67/04* (2013.01)

(58) Field of Classification Search
CPC ..... A61K 31/775; A61K 9/7023; C08G 67/04; C08G 73/02
USPC .................. 424/78.05, 78.02, 78.31; 528/176
See application file for complete search history.

(56) References Cited

U.S. PATENT DOCUMENTS 4,868,265 A *  9/1989 Gupta .............................. 528/26

OTHER PUBLICATIONS

Luppi et al. (Drug Delivery, pp. 239-244, Published 2003).*
Hosoya et al. (Chem. Pharm. Bull., pp. 882-885, Published 1998).*
Su et al. (Journal of Nanoscience and Nanotechnology, vol. 10, pp. 6369-6375, Published 2010).*
Langer et al. (Pharmaceutical Research, vol. 9, No. 10, Published 1992, pp. 1279-1283).*

* cited by examiner

*Primary Examiner* — Richard Schnizer
*Assistant Examiner* — Alma Pipic

(57) ABSTRACT

The present invention relates to a protective agent suitable to protect the human skin against toxic materials, particularly against chemicals with nucleophilic sites. The active moiety is a polyanhydride derivative. The active transdermal retardant offers a barrier property and chemically and/or physically reacts with harmful chemicals to decrease percutaneous absorption. In the preferred embodiments, polyanhydride in its low molecular weight form reduced flux of nicotine and nitrofurazone significantly. Additionally, polyanhydride in its high molecular weight form prevented nicotine absorption and decreased nitrofurazone permeation dramatically. Moreover, the polyanhydride in its high molecular weight form reduced nitroglycerin flux to a lesser extent.

2 Claims, 6 Drawing Sheets

Figure 1:
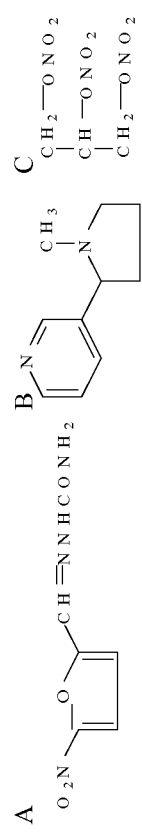
Figure 2:
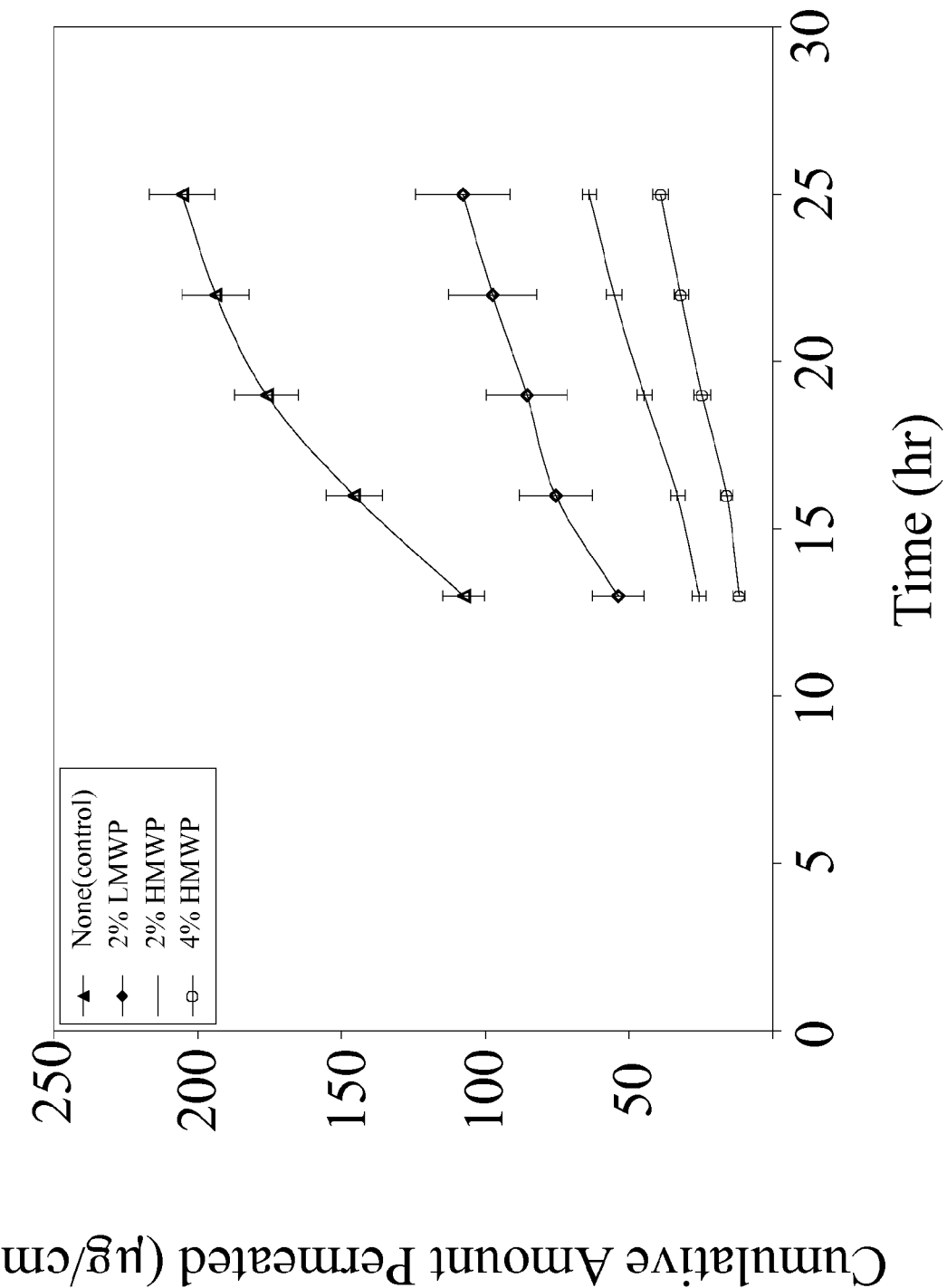
Figure 3:
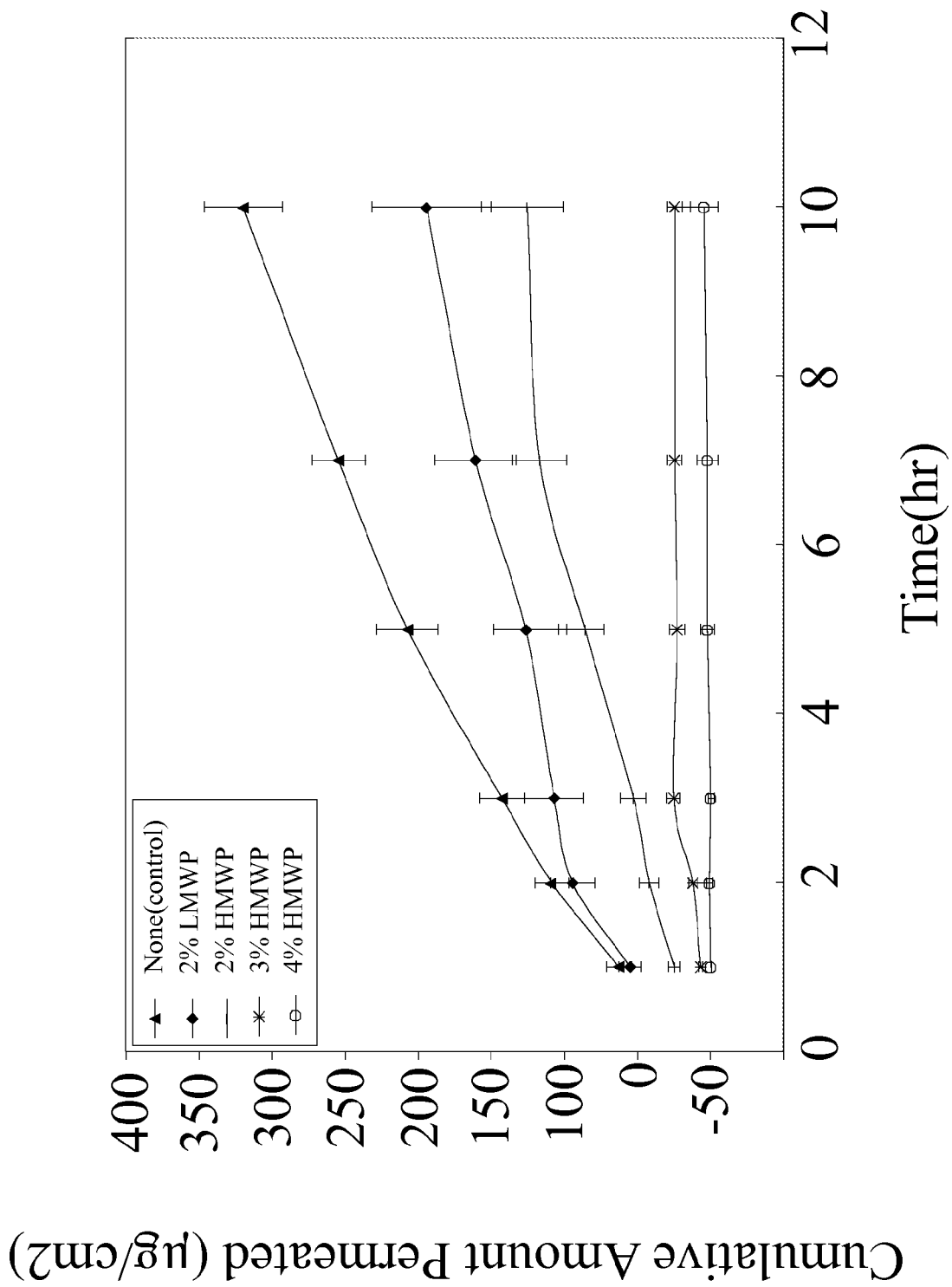

POLY(CPP-SA) ANHYDRIDE AS A REACTIVE BARRIER MATRIX AGAINST PERCUTANEOUS ABSORPTION OF TOXIC CHEMICALS

The current application claims a priority to the U.S. Provisional Patent application Ser. No. 61/453,640 filed on Mar. 17, 2011.

FIELD OF THE INVENTION

The present invention generally relates to application of a polyanhydride polymer as a transdermal retardant, which can decrease and even prevent percutaneous absorption of chemicals specifically those with nucleophilic sites. This interactive polyanhydride polymer and its family is applied prior to exposure on the skin to provide a protective barrier against chemicals.

BACKGROUND OF THE INVENTION

The skin is our largest organ and forms a fascinating and unique interface between us and the outside world. The stratum corneum, the outermost keratinized layer of thick-walled epidermal cells, is the most important, as this serves as the barrier to both the ingress of chemicals and other agents, microorganisms and dangerous substances, and the egress of water. However, the skin is not a total barrier and transdermal absorption can play a considerable role in the internal exposure of persons exposed to hazardous substances. Some chemicals are more toxic topically than orally, at least in animals. Furthermore, many compounds are absorbed to a greater degree from the skin than orally.

Dermal exposure to chemicals occurs in a wide variety of occupations, spanning agriculture, manufacturing, and industrial fields. Pesticides, solvents, and polycyclic aromatic hydrocarbons are some of the main chemical groups that have been recognized as posing health problems by dermal absorption. Due to pesticides, low volatility, and persistence, the amount of material inhaled is likely to be low unless a particularly vigorous application results in significant aerosol formation. Workers in market gardens and greenhouses can experience high dermal exposures during application or harvest where handling of vegetation coated with pesticide residues takes place. Despite widespread use of solvents, they are able to irritate and permeate the skin and affect a number of target organs within the body, including the kidneys, liver, and nervous system. As solvents tend to be volatile, their toxicity may principally result from inhalation of vapor. However, the highly lipophilic nature of most solvents can also result in dermal uptake when deposited on the skin. On the other hand, chronic exposure to solvents, which is inevitable in many occupations, may lead to an impairment of the skin barrier, so toxic substances are allowed to reach the reservoir of the stratum corneum, or even deeper layers of the skin. Skin represents a significant route of entry for many chemical warfare agents, including sulphur mustard (a skin damaging agent) and VX (an anticholinesterase or "nerve" agent) which represent a potential hazard to both public service and civilian populations and have allegedly been used by military and terrorist organizations. Many other materials may also be absorbed through the skin in significant amounts. These include mercury, isocyanates, polychlorinated biphenyls, acrylates, and pharmaceutical products such as steroids and nicotine.

On the other hand, percutaneous absorption can be increased in various ways, such as by the application of skin product on damaged skin, heat, and other mechanisms that all can worsen the problem. In this view, personal protective equipments, including specific suits, face masks, gloves and overboots, provide an efficient protection against the liquid and vapor forms of most toxic chemicals. However, due to their relative tightness, protective equipments may induce physical and heat stress. Moreover, many gloves do not resist the penetration of low molecular weight chemicals. Some allergens are soluble in rubber gloves and can penetrate the glove and induce severe dermatitis. Furthermore, the glove membrane can be structurally modified by a solvent; this may lead to changes in permeation behavior. For all these reasons, the "topical skin protectant" strategy has been adopted. Theoretically, skin barrier creams retard or even prevent the penetration into the skin. These creams can be seen as reinforcing the natural barrier function of the skin and they are developed to complement or replace protective equipments. However, different studies have revealed that often barrier creams do not fulfill their protecting behavior completely. It has been shown that barrier creams can be considered to give poor skin protection against the organic solvents investigated. Even some studies demonstrated penetration enhancement of the model penetrants through skin treated with barrier creams compared to untreated skin. It is for these reasons that there have been attempts to improve their efficacy. Special effort has been put on developing active substances that reduce percutaneous absorption of hazardous materials. It has been shown that beta-cyclodextrins may be usefully incorporated into a barrier formulation to reduce percutaneous absorption of toxic materials on occupational exposure. Permeation retardation may be due to complexation. In another study, a barrier cream coded as HP01 contains reactive protectants that chemically react with sulphur mustard. It was also shown that β-cyclodextrin and polyethylene glycol 1540 decreased the permeation of nitroglycerin significantly by about 2-4 times. The retardation effect is possibly due to hydrogen bonding between the model penetrant and the interacting polymers.

DESCRIPTIONS OF PRIOR ART

EP0223524B1 is an adhesive bandage composed of a mixture of polyanhydride and a drug used to protect a wound and deliver the drug transdermally. The adhesive film-like material is 5-500 microns thick, contains a plasticizer, and contains 50% of water by weight. The function of the invention is to form an adhesive coat on a wound and to facilitate healing thereof with the incorporated drug. Unlike the present invention, the prior art contains a pharmaceutically active agent to facilitate wound recovery.

EP200508B1 is an adhesive oral bandage comprising a soft adhesive film that is composed of an anhydride polymer. Similar to the first prior art, this prior art also contains a pharmaceutically active agent. This prior art, however, only adheres to the oral mucosa and not the entire skin organ.

SUMMARY OF THE INVENTION

An objective of the present invention is to provide a topical skin retardant which can retard percutaneous permeability and absorbability of chemical hazards. The topical skin retardant is composed a single polyanhydride derivative polymer named poly(1,3-bis(p-carboxyphenoxy)propane-sebacic acid) in low molecular weight polymer (LMWP) form and high molecular weight polymer (HMWP) form. The chemical toxins or penetrants used in this disclosure are nitrofurazone, nicotine and nitroglycerin. These penetrants have been used to illustrate the efficacy of a polyanhydride and its family as a transdermal retardant. The above-mentioned object and other objects of the present invention will be apparent from the detailed description provided hereinafter.

In one embodiment, the objectives of the present invention have been met by decreasing percutaneous permeability and absorption of active ingredients comprising high percutaneous permeability:
(a) the three model penetrants are nitrofurazone, nicotine, and nitroglycerin, of which the first two have nucleophilic sites and
(b) the potential percutaneous retardants selected were LMWP and HMWP, In a second embodiment, the effect of increasing concentration of retardants on percutaneous permeability and absorption of active ingredients with high percutaneous absorption comprising:
(a) the model penetrants are nitrofurazone, nicotine, and
(b) LMWP and HMWP concentration varied from 1 to 4% W/V (100 µl/cm2).

In a third embodiment, the effect of penetrant concentration on the retardation effect of LMWP and HMWP:
(a) the model penetrant is nitrofurazone and nitrofurazone concentration varied from saturated solution to 100 µg/ml and
(b) the potential percutaneous retardants selected were LMWP and HMWP.

As it was reported, the polymer used in this study is compatible in the implant form in human, let alone topical use, which makes it superior to other available skin retardants. It is non-toxic and safe for use, as shown by testing in animals and in humans (35). A quantity of just around 7 ml of 4% HMWP is sufficient for one application over 20% of body surface. It is worth mentioning the retardation effect reported here, through application of LMWP and HMWP, which have a molecular weight of 15000 and 75000, respectively. However we developed a method to synthesize the polyanhydride polymer with a molecular weight of up to 300000 (data not shown) which could significantly improve the retardation effect and chemical and physical barrier properties of the studied polymer.

The polymer can be considered to give good skin protection against other materials with potentially toxic effects which contain nucleophilic sites. Isocyclic amines (like aniline, nitroaniline, toluidine, xylidines, anisidine, N-methylaniline, N,N-dimethylaniline, p-phenylenediamine, β-naphthylamine and benzidine) are widely-used industrial chemicals in the production of dyes, pharmaceuticals, pesticides and rubber, etc. Several isocyclic amines have been classified as human carcinogens. The uptake of isocyclic amines at the workplace occurs by inhalation and percutaneous absorption. Hydrazine and its derivatives, such as dimethylhydrazine and phenylhydrazine, rapidly penetrate the skin and these compounds are possible carcinogens. They should be regarded as skin exposure hazards. Morpholine and N-ethylmorpholine are primary irritants that are also suspected of possible carcinogenicity. Dioxane may rapidly penetrate the skin. Due to the systemic toxicity and potential carcinogenicity, dioxane should be regarded as a skin absorption hazard (36). The novel characteristics of the present invention together with the above described objects will be more clearly understood according to the detailed explanation and embodiments of the present invention herein below.

BRIEF DESCRIPTION OF THE FIGURES

FIG. 1 illustrates chemical structure of model penetrants (a: nitrofurazone, b: nicotine, c: nitroglycerin).

FIG. 2 illustrates the cumulative penetrated amounts of nitrofurazone from an aqueous solution (200 μg/ml) through rat skin, with or without LMWP and HMWP.

FIG. 3 illustrates the cumulative penetrated amounts of nicotine from aqueous solution (500 μg/ml) through rat skin with or without LMWP and HWWP.

FIG. 4 illustrates the cumulative penetrated amounts of nitroglycerin from aqueous solution (200 μg/ml) through rat skin with or without LMWP and HMWP.

FIG. 5 illustrates the general structure of polyanhydride.

FIG. 6 illustrates the chemical structure of poly(1,3-bis(p-carboxyphenoxy)propane-sebacic acid)

DETAILED DESCRIPTION OF THE INVENTION

All illustrations of the drawings are for the purpose of describing selected versions of the present invention and are not intended to limit the scope of the present invention.

Polyanhydrides are a class of biodegradable polymers characterized by anhydride bonds that connect repeat units of the polymer backbone chain. The main application of polyanhydrides is in the medical device and pharmaceutical industry. The characteristic anhydride bonds in polyanhydrides are usually decomposed in water. This decomposition results in two carboxylic acid groups which are biodegradable components easily metabolized by the body. Biodegradable polymers such as polyanhydrides are capable of releasing physically entrapped or encapsulated drugs by well-defined kinetics. Due to their biocompatibility and drug encapsulating properties, polyanhydrides are ideal polymers used in drug delivery. Therefore, the majority of prior art thoroughly exploited the drug delivery aspect of polyanhydrides. For example, prior art EP0223524B1 and EP0200508B1 are dermal and oral bandages that utilize a polyanhydride as a drug delivery component. The present invention, however, utilizes a polyanhydride to stop chemical absorption into the skin organ and membranes. Additionally, these prior art utilize polycarboxylic acid polymer alone or with maleic anhydride. The present invention, however, utilizes only a single polyanhydride polymer.

The present invention is a transdermal retardant composed of a single polyanhydride derivative polymer named poly(1,3-bis(p-carboxyphenoxy)propane-sebacic acid) in low molecular weight polymer (LMWP) forms and high molecular weight polymer (HMWP) forms. The polyanhydride derivative polymer named poly(1,3-bis(p-carboxyphenoxy)propane-sebacic acid) has the chemical structure shown in FIG. 6, where m and n are integers from 2 to 200. Moreover, the polyanhydride derivative polymer named poly(1,3-bis(p-carboxyphenoxy)propane-sebacic acid) has the molecular weights ranging from 15000 to 75000. The transdermal retardant comprises not only the aforementioned polyanhydride derivative, but also various variations of the poly(1,3-bis(p-carboxyphenoxy)propane-sebacic acid) and its polyanhydride family, which has the general chemical structure shown in FIG. 5, where R is a linear or branched organic moiety, and m and n are integers from 2 to 200 The polymer has been used as a model from polyanhydride family as a transdermal retardant. The creation of the transdermal retardant is claimed along with methods of preparing and applying the transdermal retardant. The transdermal retardant has been manufactured using the solvent casting method for preparation of an invisible nanofilm on the skin.

The method of preparing and applying the transdermal retardant commences with mixing the transdermal retardant with chloroform and ether to formulate the final product, wherein 2% and 4% w/v of the transdermal retardant is mixed in chloroform. Subsequently, the final product is applied to skin and allowed the chloroform to evaporate in warm air in less than 10 minutes. Finally, the transdermal retardant is allowed to settle into skin while chloroform and ether evaporate. In the preferred embodiment, the thickness of the transdermal retardant is 100 μl/$cm^2$ or 1 millimeter. Chloroform serves as a solvent and a carrier of the polyanhydride polymer. Additionally, ether serves as a stabilizer to the transdermal retardant. The transdermal retardant may be formulated in various forms such as solvent, aerosol and semisolid.

As reported in Summary of Invention and Examples thereinafter, both low molecular weight polymer (LMWP) and high molecular weight polymer (HMWP) forms of the poly (1,3-bis(p-carboxyphenoxy)propane-sebacic acid) retard transdermal diffusion of nitrofurazone, nicotine, and nitroglycerin. Therefore, the results illustrate the efficacy of the polyanhydride as a transdermal retardant.

EXAMPLE 1

The retardation effect of LMWP and HMWP against the percutaneous absorption of nitrofurazone through rat skin is demonstrated in this example. The study was performed ex vivo on a male Wistar rat skin. Each rat was euthanized with chloroform vapor and the abdominal hair was gently removed with an electric clipper. The abdominal skin excised as full-thickness and was cleaned of extraneous tissue. For the experiments the skin was placed in home-made vertical Franz-type glass diffusion cells, while the stratum corneum was facing the donor compartment. Each diffusion cell was allowed to equilibrate with the receptor fluid for 24 hrs prior to experiments at ambient temperature. Our preliminary studies showed that distilled water cannot provide a perfect sink condition for nitrofurazone, therefore, two other systems of a) Tween 20 aqueous solution (1% w/v) and b) a mixture of distilled water, acetonitrile and triethylamine buffer (79:20:1) were investigated and the latter was chosen as the receptor phase for nitrofurazone. This mixture is suggested as mobile phase for HPLC assay of nitrofurazone by USP (35) and the effect of this mixture as an enhancer was investigated here. Results showed that this system did not change the nitrofurazone flux through rat skin when used in both donor and receptor phases. This solution could provide sink condition. Solubility of nitrofurazone in this receptor phase was measured to be 668 μg/ml.

After the 24 hr equilibration phase, receptor phases were replaced with fresh phases and its temperature was set at 37.0±0.1° C. to provide surface temperature of 32° C. The retardants were applied to the donor phase as 2 and 4% w/v solution in chloroform (100 μl/$cm^2$) and the solvent evaporated in less than 10 min using warm air. The systems were left to settle and the final residues of chloroform to evaporate (as much as possible). Permeants were then applied to the donor phase as aqueous solutions of 200 μg/ml. Interval sampling was performed for 24 hrs. Donor phase was replaced with fresh one at 13 hours. Permeated nitrofurazone of all samples was measured by UV spectrophotometry at 385 nm. The results are shown in FIG. 2 and summarized in Table 1 below.

TABLE 1

Effects of low (LMWP) and high (HMWP) molecular weight polyanhydride on permeation of nitrofurazone through rat skin (mean ± SD, n = 3-5).

| Treatment | Flux (μg/$cm^2$/hr) | Flux FRR[a] | P-value | Lag-time: Lag-time (hr) | Lag-time: LER[b] | Lag-time: P-value | $Q_{24}$(μg/$cm^2$)[c] |
|---|---|---|---|---|---|---|---|
| None (control) | 11.44 ± 1.62 | 1 | | 3.53 ± 0.45 | | | 205.41 ± 28.02 |
| 2%(W/V) LMWP | 5.31 ± 1.69 | 2.16 | 0.000 | 2.94 ± 1.04 | 0.83 | 0.244 | 107.63 ± 32.60 |
| 4%(W/V) LMWP | 4.44 ± 1.50 | 2.58 | 0.000 | 1.77 ± 1.52 | 0.50 | 0.023 | 56.72 ± 30.54 |
| 2%(W/V) HMWP | 3.67 ± 0.04 | 3.12 | 0.000 | 6.97 ± 1.53 | 1.97 | 0.000 | 63.57 ± 5.46 |
| 4%(W/V) HMWP | 2.45 ± 0.45 | 4.67 | 0.000 | 9.01 ± 1.86 | 2.55 | 0.000 | 38.82 ± 5.63 |

[a]FRR: Flux retardation ratio (control/treated)
[b]LER: Lag time elongation ratio (treated/control)
[c]Q24: cumulative amount of nitrofurazone permeated after 24 hr
[d]$k_p$: permeability coefficient As shown in Table 1 above and FIG. 2, nitrofurazone showed a permeation flux of 11.4±1.6 (μg/$cm^2$/hr) and lag-time of 3.5±0.4 (hr) in control samples. Retardant treatment decreased nitrofurazone flux and increased its lag-time up to 4.7 and 2.6 times, respectively. The effects of both polymers at all concentration on nitrofurazone flux retardation (2.2-4.7 times) were statistically significant (p<0.00). For the lag-time however, while LMWP at 2% did not show a significant effect (p>0.05), HMWP at both 2% and 4% was able to increase the lag time significantly (p<0.00) by about 2.0 and 2.6 times, respectively. In studies with LMWP, there was no delay in the appearance of penetrants in the receptor compartment, which indicates that the preparation did not form a physical barrier on the skin. However, after pretreatment with HMWP, the appearance of penetrants was delayed. These results suggest that this composition also acted as a physical barrier.

EXAMPLE 2

The retardation effect of LMWP and HMWP against the percutaneous absorption of nicotine through rat skin is demonstrated in this example. The procedures in Example 1 were repeated using distilled water as the receptor phase and aqueous nicotine solution of 500 μg/ml as the donor phase. Permeated nicotine of all samples was measured by UV spectrophotometry at 260 nm. Table 2 and FIG. 3 summarize the effects of different concentrations of low and high molecular weight polymers on percutaneous absorption of nicotine through rat skin at 32° C.

TABLE 2

Effects of low (LMWP) and high (HMWP) molecular weight polyanhydride on permeation of nicotine through rat skin (mean ± SD, n = 3-5).

| Treatment | Flux (μg/cm²/hr) | Flux FRR[a] | P-value | $Q_{10}$(g/cm²)[b] | $k_p$(cm/hr * $10^2$)[c] |
|---|---|---|---|---|---|
| None (control) | 40.00 ± 6.97 | 1.00 | — | 319.82 ± 52.64 | 8.00 ± 1.39 |
| 2%(W/V) LMWP | 19.57 ± 3.07 | 2.04 | 0.006 | 193.88 ± 74.83 | 3.91 ± 0.61 |
| 2%(W/V) HMWP | 15.62 ± 6.70 | 2.56 | 0.001 | 116.63 ± 45.10 | 3.12 ± 1.34 |
| 3%(W/V) HMWP | 9.37 ± 3.43 | 4.27 | 0.000 | 24.48 ± 8.81 | 1.87 ± 0.69 |
| 4%(W/V) HMWP | NO[d] | — | — | NO | NO |

[a]FRR: Flux retardation ratio (control/treated)
[b]$Q_{10}$: cumulative amount of nicotine permeated within 10 hrs
[c]$k_p$: permeability coefficient
[d]NO: not observed Control (untreated) skin exhibited a nicotine steady-state flux of 40.00±6.97 μg/cm²/hr. The presence of polymeric film from 2% (W/V) LMWP reduced the flux of nicotine significantly (P=0.006) by about 2 times. Application of 2% HMWP showed a higher retardation effect for permeation of nicotine (2.6 times, P=0.001). When the HMWP concentration was increased to 3%, it showed a low but detectable amount of nicotine in the receptor phase at 2 and 3 hours, which stayed constant until the end of the experiments. At 4%, HMWP stopped permeation of nicotine through rat skin completely, as no nicotine was observed in the receptor compartment throughout the experiment.

EXAMPLE 3

It was decided here to study the effect of penetrant concentration on the retardation effect of LMWP and HMWP, based on the hypothesis that the complexation mechanism is affected by permeant concentration, while a simple barrier effect does not. As nicotine and nitrofurazone have similar sites for nucleophilic attack, only one of these permeants (nitrofurazone) was used to investigate this hypothesis. The retardation effect of LMWP and HMWP against the percutaneous absorption of 100, 200 μg/ml and saturated solutions of nitrofurazone through rat skin is demonstrated in this example. An absorption rate of 5.11±1.39 μg/cm²/hr was measured with 100 μg/ml nitrofurazone in aqueous solution, and this increased further to 11.44±1.62 μg/cm²/hr and 18.24±1.51 μg/cm²/hr with 200 μg/ml and saturated nitrofurazone in aqueous solution. This model penetrant also showed concentration-dependent lag time profile. The profile of the relationship between flux retardation ratio and concentration of nitrofurazone indicated that flux retardation ratio increased significantly with decreasing concentration of nitrofurazone (Table 3). The same profile, although to a lesser extent, was observed about HMWP between lag time elongation ratio and nitrofurazone concentration (Table 4).

TABLE 3

Effects of different concentrations of nitrofurazone on flux retardation efficacy of low (LMWP) and high (HMWP) molecular weight polyanhydride through rat skin (mean ± SD, n = 3-5).

| | Flux (μg/cm²/hr) | | | | | |
|---|---|---|---|---|---|---|
| Nitrofurazone concentration | None(control) | 2%(W/V) LMWP | FRR[a] | P-value | 2%(W/V) HMWP | FRR[a] | P-value |
| saturated | 18.24 ± 1.51 | 14.28 ± 1.90 | 1.28 | .006 | 12.31 ± 3.24 | 1.48 | 0.009 |
| 200 μg/ml | 11.44 ± 1.62 | 5.31 ± 1.69 | 2.16 | .000 | 3.67 ± 0.04 | 3.12 | 0.000 |
| 100 μg/ml | 5.11 ± 1.39 | 1.69 ± 0.48 | 3.02 | .000 | 1.44 ± 0.31 | 3.55 | 0.000 |

[a]FRR: Flux retardation ratio (control/treated)

TABLE 4

Effects of different concentrations of nitrofurazone on lag time elongation efficacy of low (LMWP) and high (HMWP) molecular weight polyanhydride through rat skin (mean ± SD, n = 3-5).

| | Lag time (hr) | | | | | |
|---|---|---|---|---|---|---|
| Nitrofurazone concentration | None (control) | 2%(W/V) LMWP | LER[a] | P-value | 2%(W/V) HMWP | FRR[a] | P-value |
| saturated | 1.44 ± 0.56 | 2.00 ± 0.69 | 1.39 | 0.241 | 2.75 ± 0.71 | 1.92 | 0.012 |
| 200 g/ml | 3.53 ± 0.45 | 2.94 ± 1.04 | 0.83 | 0.244 | 6.97 ± 1.53 | 1.96 | 0.000 |
| 100 g/ml | 4.17 ± 0.62 | 4.82 ± 4.43 | 1.16 | 0.745 | 6.51 ± 0.62 | 1.56 | 0.000 |

[a]LER: Lag time elongation ratio (treated/control)

EXAMPLE 4

Figure 4:
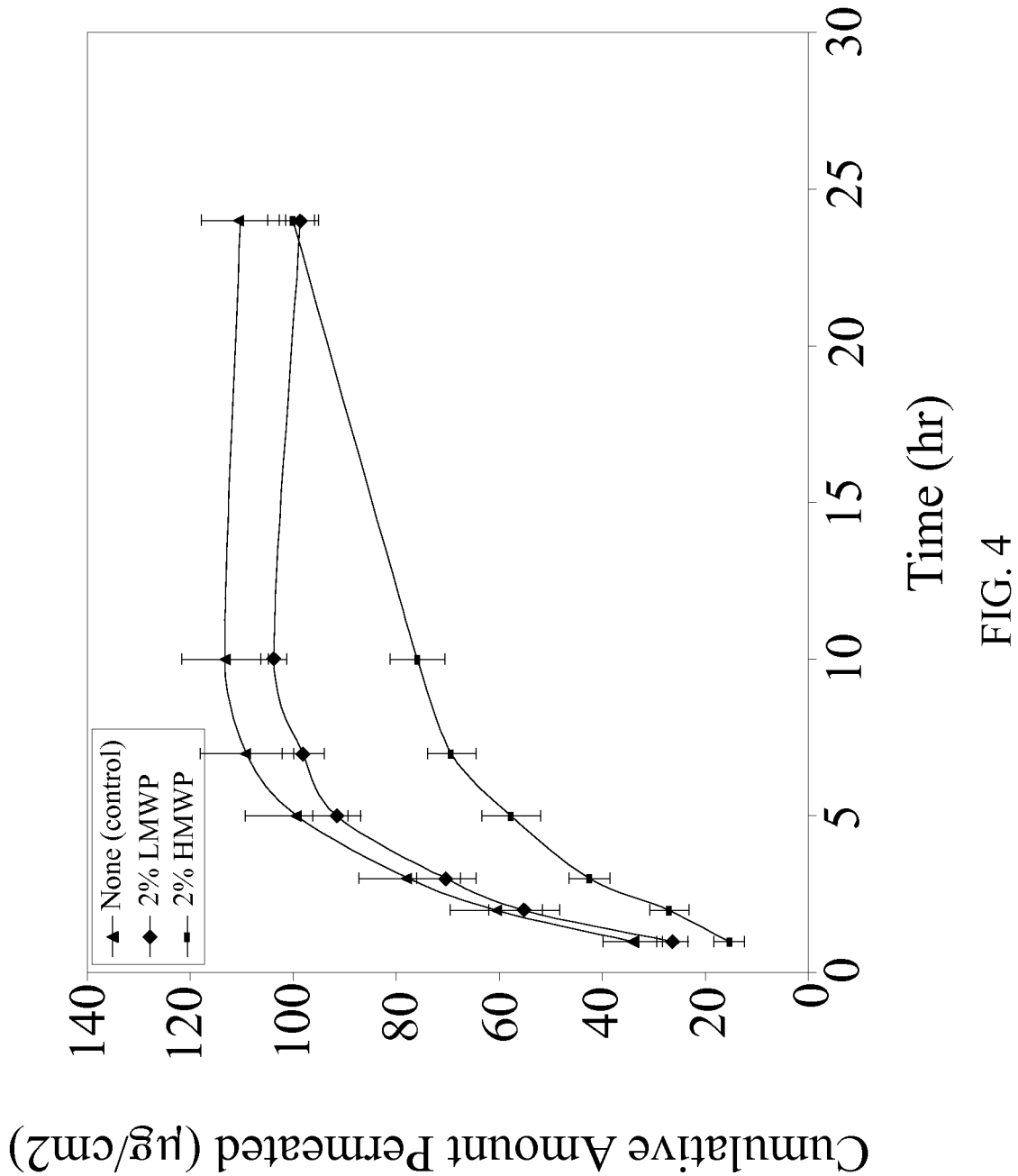
Figure 5:
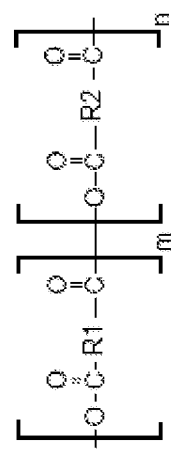
Figure 6:
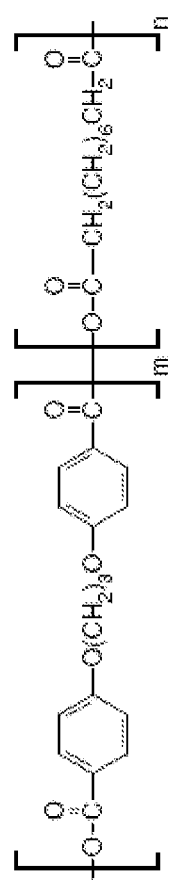

The retardation effect of LMWP and HMWP against the percutaneous absorption of nitroglycerin through rat skin is demonstrated in this example. The procedures in Example 2 were repeated using aqueous nitroglycerin solution of 200 µg/ml as the donor phase. The amount of permeated nitroglycerin was measured using the Bell spectrophotometric method (37). Nitroglycerin was chosen as a model penetrant that does not have nucleophilic sites. Table 5 and FIG. 4 summarize the effect of low and high molecular weight polymer on percutaneous absorption of nitroglycerin through rat skin.

TABLE 5

Effects of low (LMWP) and high (HMWP) molecular weight polyanhydride on permeation of nitroglycerin through rat skin (mean ± SD, n = 3-5).

| Treatment | Flux Flux(µg/cm$^2$/hr) | FRR[a] | P-value | $Q_{10}$(µg/cm$^2$)[b] | kp (cm/hr * 102)[c] |
|---|---|---|---|---|---|
| None (control) | 21.42 ± 5.77 | 1.00 | — | 110.20 ± 18.47 | 10.71 ± 2.88 |
| 2%(W/V) LMWP | 20.99 ± 5.03 | 1.02 | 0.893 | 98.58 ± 6.86 | 10.50 ± 2.30 |
| 2%(W/V) HMWP | 13.59 ± 3.52 | 1.58 | 0.036 | 99.93 ± 9.88 | 6.80 ± 2.12 |

[a]FRR: Flux retardation ratio (control/treated)
[b]$Q_{10}$: cumulative amount of nitroglycerin permeated within 10 hrs
[c]$k_p$: permeability coefficient Penetration of nitroglycerin was not significantly changed in the presence of polymeric film from 2% (W/V) LMWP (P=0.803). However, application of 2% HMWP led to a decrease of flux by 1.6 (P=0.036). Cumulative amount absorbed after 24 hrs in presence of LMWP and HMWP has not changed compared to untreated skin (P=0.293). In this example the utilization of higher molecular weight of this polymer which was synthesized in our lab (data not shown) could be highly advantageous.

Although the invention has been explained in relation to its preferred embodiment, it is to be understood that many other possible modifications and variations can be made without departing from the spirit and scope of the invention as hereinafter claimed.

What is claimed is:

1. A transdermal retardant comprising poly(1,3-bis(p-carboxyphenoxy)propane-sebacic acid) having a molecular weight between 15000 and 300000; chloroform; and ether, wherein poly(1,3-bis(p-carboxyphenoxy)propane-sebacic acid) is present in a concentration of 2% to 4% w/v of the chloroform.

2. A method of preparing and applying a transdermal retardant claimed in claim 1, comprises the steps of:
    (a) mixing poly(1,3-bis(p-carboxyphenoxy)propane-sebacic acid) with chloroform and ether to obtain a final product wherein poly(1,3-bis(p-carboxyphenoxy)propane-sebacic acid) is present in a concentration of 2% to 4% w/v of the chloroform;
    (b) applying the final product to skin and evaporating chloroform within less than 10 minutes; and
    (c) allowing the transdermal retardant to settle into skin during evaporation of chloroform and ether residues.

* * * * *